United States Patent [19]

Larkin

[11] 4,397,442

[45] Aug. 9, 1983

[54] IN-LINE SLEEVE VALVE

[75] Inventor: Mark E. Larkin, Lindenhurst, Ill.

[73] Assignee: Abbott Laboratories, North Chicago, Ill.

[21] Appl. No.: 223,669

[22] Filed: Jan. 9, 1981

[51] Int. Cl.$^3$ .............................................. F16K 31/00
[52] U.S. Cl. .................................... 251/342; 251/348;
    251/353; 251/354; 137/68 R; 604/33; 604/249;
    604/905
[58] Field of Search ............... 251/342, 347, 348, 353,
    251/354; 128/213 A, 274

[56] References Cited

U.S. PATENT DOCUMENTS

| Re. 25,807 | 6/1965 | Raehs | 251/342 X |
|---|---|---|---|
| 2,862,648 | 12/1958 | Cooksley | 251/353 X |
| 3,144,179 | 8/1964 | Gildone | 251/353 X |
| 3,521,859 | 7/1970 | Gronemeyer | 251/353 |
| 3,547,401 | 12/1970 | Beall | 251/342 X |
| 3,699,580 | 10/1972 | Joseph | 403/329 X |
| 3,707,972 | 1/1973 | Villari | 128/247 UX |
| 4,117,859 | 10/1978 | Illy | 251/342 X |

Primary Examiner—Harold W. Weakley
Attorney, Agent, or Firm—Robert S. Beiser; Robert L. Niblack

[57] ABSTRACT

An improved in-line sleeve valve comprises a modular tubular port having a stationary plug concentrically supported therein and a reciprocating tubular sleeve arranged for sealing against the stationary plug. A resilient, flexible flange connects the tubular sleeve and the tubular port. The flange is sufficiently elastic to allow easy manual displacement of the sleeve from the tubular stationary plug in order to allow the flow of liquid, but is biased in a first direction so as to return the tubular sleeve to a position abutting the stationary plug upon release thereof.

1 Claim, 9 Drawing Figures

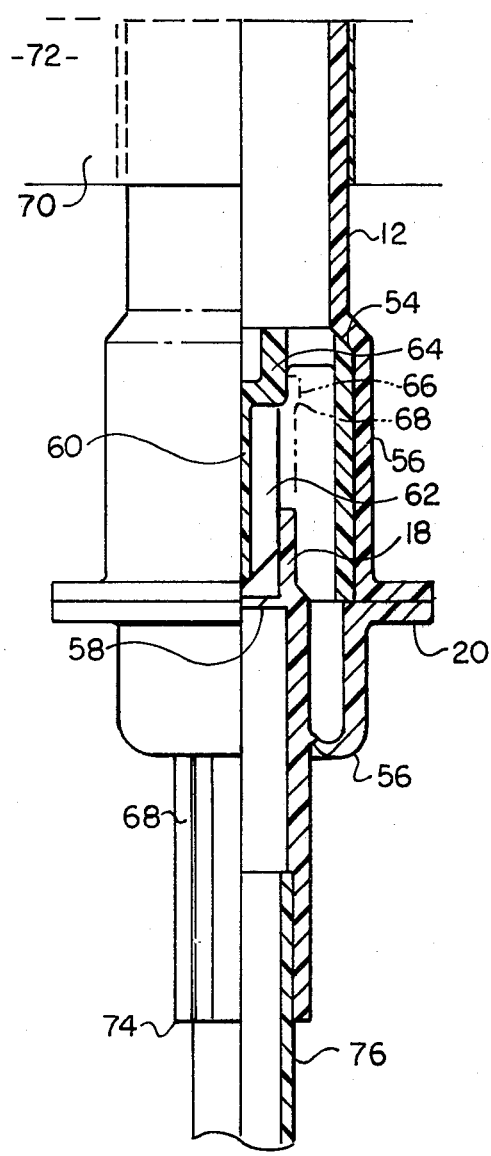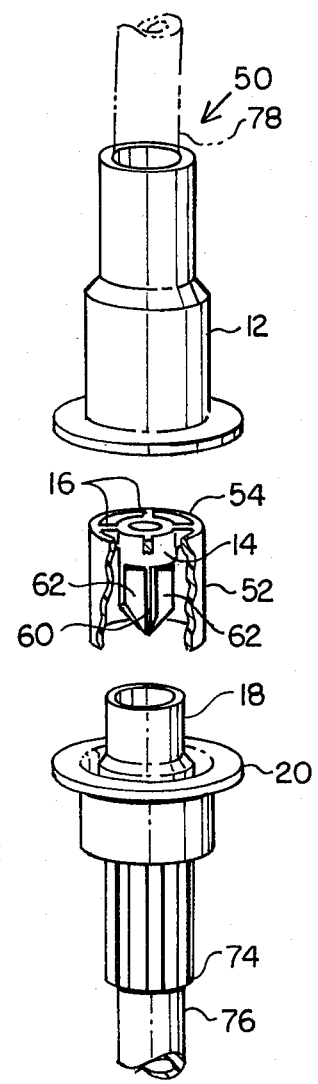
FIG. 5
FIG. 4

IN-LINE SLEEVE VALVE

BACKGROUND OF THE INVENTION

I. Field of the Invention

This invention relates to an improved in-line sleeve valve and more particularly to a two-piece valve having a resilient, flexible flange connecting the two tubular pieces and biasing them in a sealed position.

II. Description of the Prior art

A prior art search directed to the subject matter of this application uncovered the following U.S. Pat. Nos:
234,735
1,423,418
1,716,802
1,958,429
2,859,932
3,219,278
3,482,785
3,547,401
3,707,972
3,823,716
4,055,179.

The advantage of the present invention over the prior art known to applicant is that it provides a positive shut-off of flow therethrough in a closed position, a relatively free, unobstructed flow therethrough when in an open position, and can be easily and rapidly resealed.

SUMMARY OF THE INVENTION

The present invention comprises an improved inline sleeve valve having a modular tubular port with a stationary plug concentrically affixed and supported therein by one or more support members. A reciprocating tubular sleeve is provided for sealable engagement with the stationary plug. Being tubular, the sleeve allows the passage of liquid therethrough when removed from the stationary plug. A resilient, flexible flange is concentrically disposed between the reciprocating tubular sleeve and the tubular port so as to seal the connection therebetween. The flange is sufficiently elastic to allow manual displacement of the tubular sleeve from the stationary plug in order to allow the flow of liquid. However, the flange is biased in a first direction so as to return the tubular sleeve to a position abutting the stationary plug upon the release thereof.

In a preferred embodiment, the previously mentioned stationary plug has a plurality of detent ribs projecting therefrom at a first end which are constructed and arranged for controlling the movement of the tubular sleeve onto the stationary plug. As a result, while the sleeve returns to its first position, it is not sealably engaged against the plug until it has been manually press-fit over the detent ribs. Conversely, the sleeve must be removed from its press-fit over the detent ribs in order to allow the flow of liquid therethrough.

In one embodiment, disposed between the stationary plug and the tubular sleeve is a frangible membrane which hermetically seals the connection therebetween. When the membrane is broken by movement of the tubular sleeve, liquid is allowed to flow therethrough.

Similarly, as an additional feature of the invention, a safety cap member may be attached to the tubular port and extend about the tubular sleeve for preventing the inadvertent movement of the tubular sleeve and consequent opening of the valve. One further additional feature of the invention is a multi-tier fitment, which may be press-fit into and connecting with a plurality of sizes of flexible tubing. The multi-tier fitment may be disposed at one end of the reciprocating sleeve or at the opposite end of the modular port assembly.

In an alternative embodiment of the invention, a pierceable membrane is affixed across the tubular sleeve so as to hermetically seal it, and a piercing pin is attached to and extends from the stationary plug, constructed and arranged for the penetration of the pierceable membrane when the tubular sleeve is moved in a first direction towards the pin. In a preferred embodiment, the piercing pin includes a plurality of fins coaxially disposed thereon, adapted for the passage of liquid along said pin upon penetration of said pierceable membrane. In order to reseal the device, the piercing pin may be pushed sufficiently through the membrane so as to engage the tubular sleeve about a tapered sealing rim concentrically disposed at the top of the piercing pin. Alternatively, in those embodiments where a piercing pin and pierceable membrane are not utilized, the tubular sleeve is simply interfitted with the sealing rim in order to maintain a hermetic seal within the valve.

In a preferred embodiment, the modular port member is sealably attached to and extends from a liquid container so as to permit the selective passage of liquid therefrom or thereto. Alternatively, the modular port may be sealably attached to a flexible tube, and the second tubular member sealably attached to a second tube, in order to permit the selective flow of liquid therebetween.

In an additional alternative embodiment, the modular tubular port member contains a sealed chamber at a second end. The reciprocating tubular sleeve is slidably sealed within this chamber. The reciprocating tubular sleeve further is sealed at the first end and has a plurality of apertures into the sleeve spaced apart from the first end. As a result, when the sleeve is moved to a second position further within the modular port, the apertures are exposed to the liquid and allow it to flow into and through the sleeve. However, when the sleeve is released, it returns to its first position and the flow of liquid is prevented.

BRIEF DESCRIPTION OF THE DRAWINGS

FIG. 4 of the drawings is a perspective view, partially broken away, of an alternate embodiment of an improved in-line sleeve valve showing in particular a piercing pin attached to the stationary plug.

FIG. 5 of the drawings is a front view, partially broken away, of the improved in-line sleeve valve of FIG. 4 showing in particular the relationship between the piercing pin and a pierceable membrane in the tubular sleeve.

DETAILED DESCRIPTION OF THE PREFERRED EMBODIMENT

Figure 3:
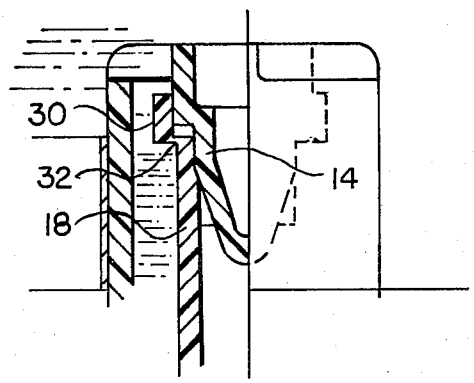
FIG. 3 of the drawings is a vertical section of a portion of the improved in-line sleeve valve of FIG. 2 showing in particular a frangible membrane between the tubular sleeve and the stationary plug of FIG. 2.

While this invention is susceptible of embodiment in many different forms, there is shown in the drawings and will herein be described in detail, several specific embodiments, with the understanding that the present disclosure is to be considered as an exemplification of the principles of the invention and is not intended to limit the invention to the embodiments illustrated.

Figure 1:
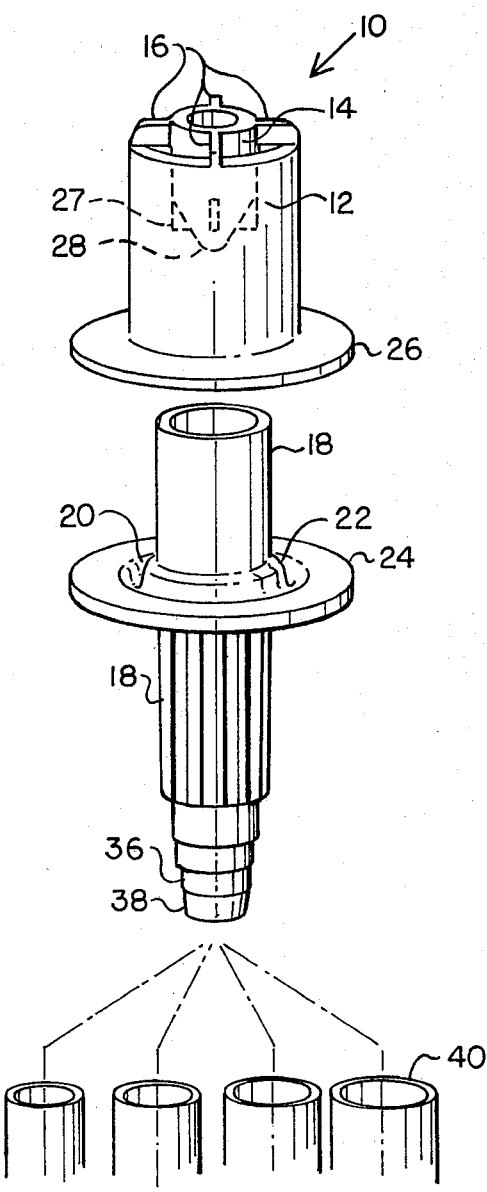
FIG. 1 of the drawings is an exploded front perspective view of an improved in-line sleeve valve.

As best seen in FIG. 1 of the drawings, improved in-line sleeve valve 10 comprises a modular tubular port 12 having a stationary plug 14 concentrically affixed to and supported within the port by a plurality of support members 16. A reciprocating tubular sleeve 18 is sized and positioned for sealable engagement with stationary plug 14 in a first position, but allows the passage of liquid through itself when in a second position disposed away from the plug.

A resilient, flexible flange 20 is concentrically disposed between the reciprocating tubular sleeve and modular tubular port 12 so as to seal the connection therebetween. In the embodiment illustrated, resilient, flexible flange 20 has a first convoluted portion 22 which is specifically designed for flexing in both directions and a substantially flat portion 24 designed for abutment with and attachment to corresponding flange 26, concentrically disposed about modular tubular port 12. In the embodiment illustrated, flanges 24 and 26 are sealed together by conventional means, such as adhesive, welding or heat sealing.

Flexible flange 20, in general, and flex convolutions, 22 in particular, are sufficiently elastic to allow easy manual displacement of tubular sleeve 18 from off of stationary plug 14. This allows the flow of liquid through modular tubular port 12 and tubular sleeve 18. However, flexible flange 20 is biased so as to resiliently return tubular sleeve 18 to its original position abutting against stationary plug 14 upon release.

In a preferred embodiment, stationary plug 14 includes a plurality of detent rib members 27 projecting from first end 28 of stationary plug 14. Ribs 27 are of the proper size and position for controlling the movement of tubular sleeve 18 onto and off of stationary plug 14. In particular, ribs 27 are sufficiently large to hinder the movement of tubular sleeve 18 onto stationary plug 14 so that the bias of flexible flange 20 is not sufficient to reseal tubular sleeve 18, but tubular sleeve 18 may be manually press-fit over ribs 27 and onto stationary plug 14 so as to seal.

As best seen in FIG. 3 of the drawings, in one embodiment, frangible membrane 30 is disposed between stationary plug 14 and tubular sleeve 18, so as to hermetically seal the connection therebetween. However, frangible membrane 30 may be broken along score line 32 so as to allow separation of tubular sleeve 18 from stationary plug 14. Tubular sleeve 18 may then be moved away from stationary plug 14.

Figure 2:
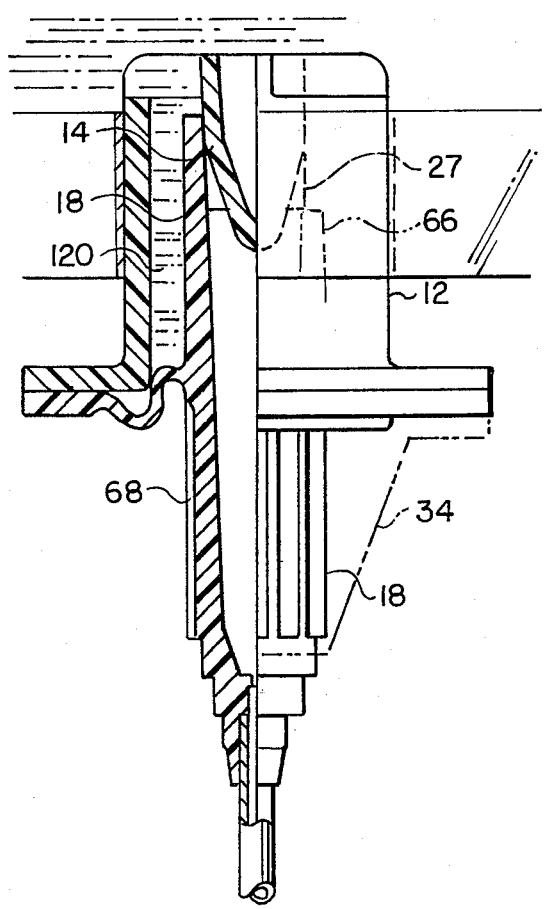
FIG. 2 of the drawings is a front view, partially broken away, of the improved in-line sleeve valve of FIG. 1 showing in particular the engagement of the tubular sleeve with a stationary plug.

As best seen in FIG. 2 of the drawings, an additional feature of the invention is a removable safety cap 34 attached to tubular port member 12 and extending about tubular sleeve member 18 so as to prevent the inadvertent movement of tubular sleeve 18 and consequent opening of valve 10 prior to the desired period of use. FIG. 2 further illustrates the interrelationship between tubular sleeve 18 and stationary plug 14.

It should be noted that all the embodiments shown, as well as other embodiments contemplated by one of ordinary skill in the art, a common feature is the use of a reciprocating tubular sleeve attached to a modular tubular port by a resilient flexible flange which allows easy manual displacement of the sleeve so as to allow the passage of liquid therethrough.

As best seen in FIGS. 1 and 2 of the drawings, improved in-line sleeve valve 10 may include multi-tier Luer fitment 36 extending from tubular sleeve 18. Luer fitment 36 is designed for press-fit into or solvent-sealing with a plurality of sizes of flexible tubing. Multi-tier Luer fitment 36 comprises a progressive series of stepped outside diameters, increasing incrementally from proximate the tip 38 of Luer fitment 36 in sequentially larger steps along tubular sleeve 18. In a preferred embodiment, the area proximate tip 38 is tapered inwardly so as to allow press-fit into a corresponding Luer lock fitting 40, to which sleeve valve 10 may be attached.

As best seen in FIGS. 4 and 5 of the drawings, in an alternative embodiment, in-line sleeve valve 10 comprises modular tubular port 12 having stationary plug 14 affixed therein. Unlike FIGS. 1 and 2, however, support member 16 extends to sleeve 52, which is tapered at first end 54 and is of an outside diameter slightly smaller than the inside diameter of portion 56 of tubular port 12. As a result, sleeve 52 may be press-fit into tubular port 12. Tubular sleeve 18 is attached to modular port 12 by resilient flange 20. However, in the embodiment illustrated, rolling diaphragm 56 extends downwardly from flange 20. Affixed across tubular sleeve 18 is a pierceable membrane 58 which hermetically seals the sleeve. Piercing pin 60 extends downwardly from stationary plug 14 and is positioned to penetrate pierceable membrane 58 when tubular sleeve 18 is moved upwardly in a first direction against piercing pin 60. In the embodiment shown, piercing pin 60 further includes a plurality of fin members 62 coaxially disposed about pin 60, and adapted for passage of liquid along the piercing pin when it has penetrated membrane 58. Alternatively, although not shown in the drawings, piercing pin 60 may have an aperture extending therethrough to allow the passage of liquid. In regard to such resealing, piercing pin 60 includes a tapered rim portion 64 proximate its first end 66 which is of the proper size for being press-fit into end 68 of reciprocating tubular sleeve 18 so as to seal it following penetration of membrane 58.

As seen in FIGS. 1 through 5, tubular sleeve 18 may include finger grip portion 68 which facilitates movement of tubular sleeve 18 upward or downward, as required. Although valve 10 may be constructed of a wide variety of materials, in a preferred embodiment tubular port 12 is constructed of polyvinylchloride, stationary plug 14 and piercing pin 60 are constructed of polypropylene, tubular sleeve 18 is constructed of polyvinylchloride, and flexible diaphragm 20 is constructed of either polyvinylchloride or resilient silicone rubber.

As best seen in FIG. 5 of the drawings, in a preferred embodiment modular tubular port 12 is sealably attached to a liquid container 70 and extends therefrom. Thus liquid 72 within liquid container 70 may be dispensed from the container as desired. Alternatively, modular tubular port 12 may be integrally formed from liquid container 70, particularly when used in blow molded PVC bags.

As seen in FIG. 4, extending from second end 74 of tubular sleeve 18 is a first flexible tube 76 which is sealably attached thereto. A second flexible tube 78 extends from modular tubular port 12. Thus, inline valve 10 connects first flexible tube 76 and second flexible tube 78.

Figure 6:
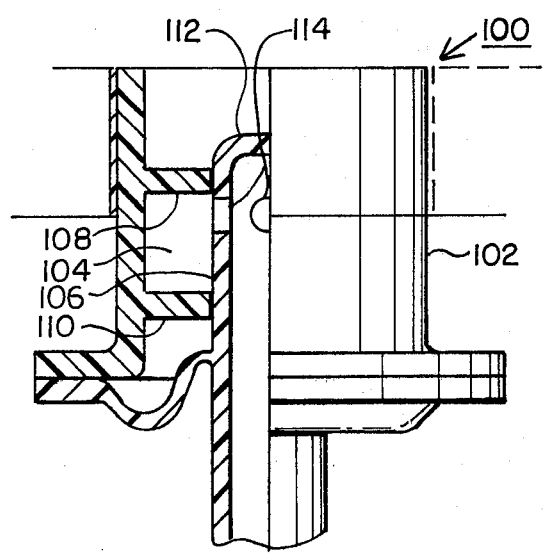
FIG. 6 is a vertical section, partially broken away, of an alternative embodiment of an improved in-line sleeve valve having a tubular sleeve slidably sealed within a chamber in the modular port, with a plurality of apertures opening into the tubular sleeve but spaced apart from the end of the tubular sleeve so as to allow the selective passage of liquid therethrough.

As best seen in FIG. 6 of the drawings, in an alternative embodiment improved in-line sleeve valve 100 comprises a modular tubular port 102 containing a sealed chamber 104 therein. Reciporcating tubular sleeve 106 is slidably sealed within chamber 104 by means of gaskets 108 and 110. Reciprocating tubular sleeve 106 is sealed at first end 112 and has a plurality of apertures 114 spaced apart from end 112 and extending into tubular sleeve 106. Thus when reciprocating tubular sleeve 106 is moved upwardly into modular tubular port 102, liquid may flow into and through said apertures 114 and thus into and through tubular sleeve 106. However, when released sleeve 106 returns to its original position with apertures 114 disposed below gasket 108 thereby resealing valve 100 and preventing the flow of liquid therethrough.

Figure 7:
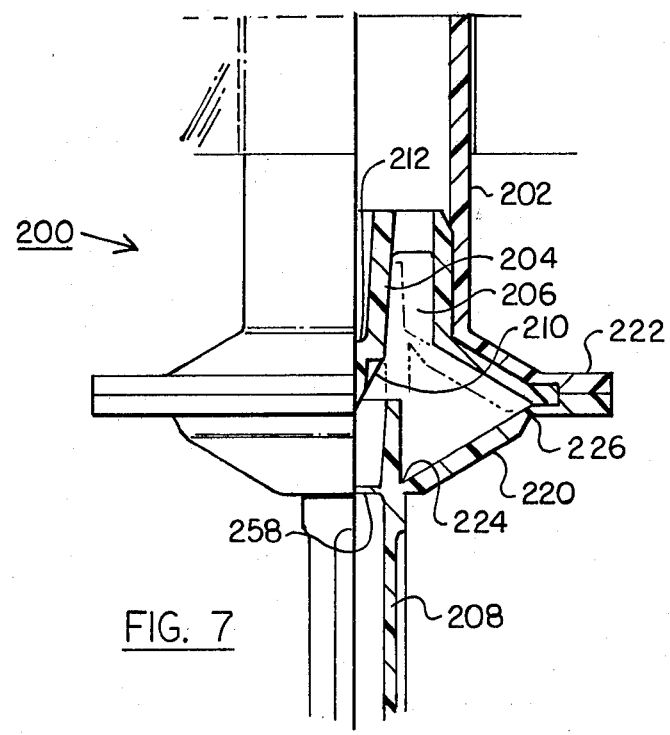
FIG. 7 of the drawings is a front view, partially in section, of an alternative embodiment of an improved inline sleeve valve having a piercing pin and an integrally hinged flexible flange.
Figures 8, 9:
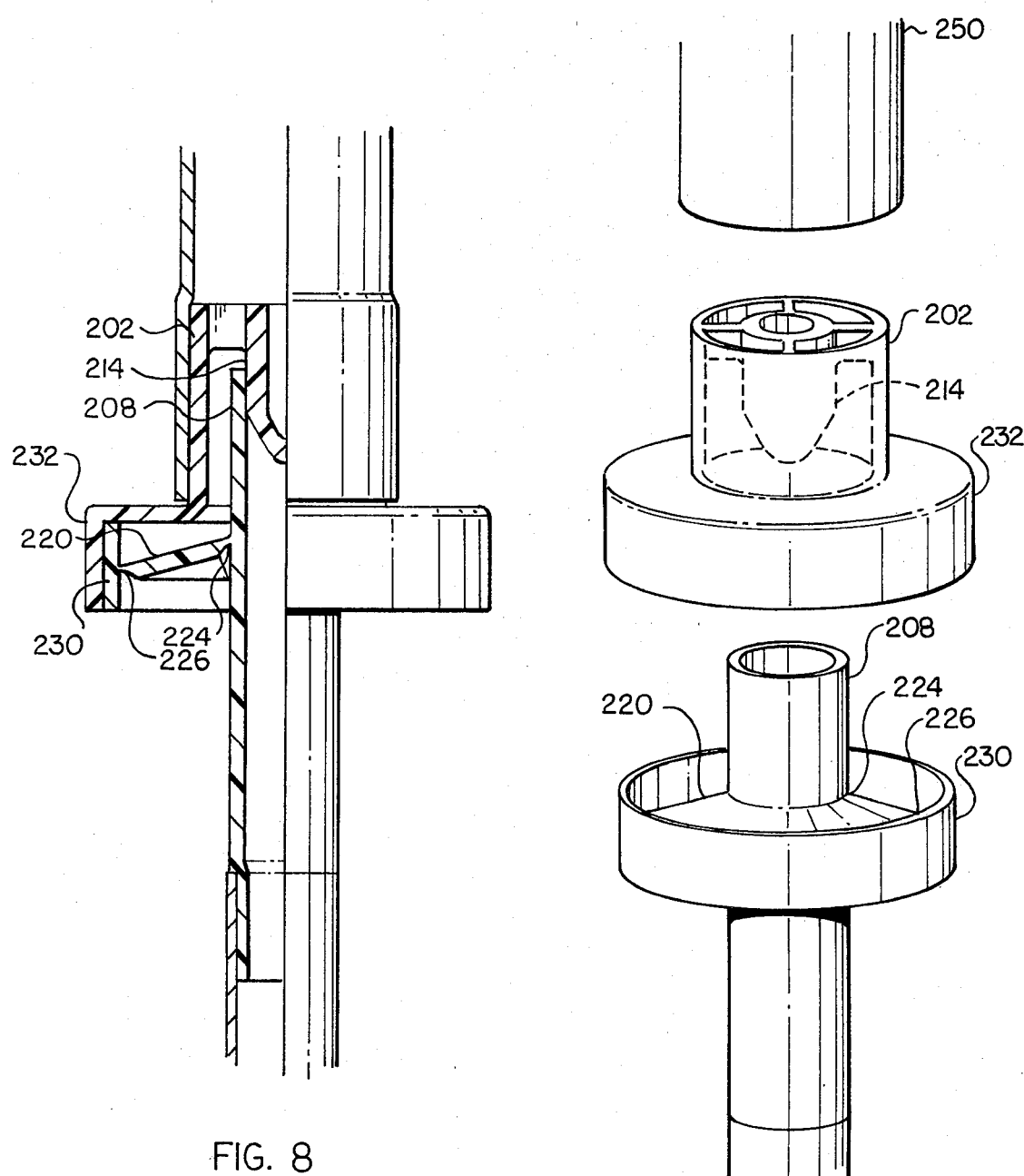
FIG. 8 of the drawings is an alternative embodiment of the sleeve valve of FIG. 7.
FIG. 9 of the drawings is a perspective exploded view of the sleeve valve of FIG. 8.

Two additional embodiments of the invention may be seen in FIGS. 7, 8 and 9. As best seen in FIG. 7, improved in-line sleeve valve 200 comprises a modular tubular port 202 having a piercing pin 204 concentrically affixed to and supported within the port 202 by support member 206. A reciprocating tubular sleeve 208 is positioned for sealable engagement with piercing pin 204 in a first position (shown in dotted lines). Affixed across tubular sleeve 208 is a pierceable membrane 258 which hermetically seals sleeve 208. Piercing pin 206 extends downwardly in port 202 and is positioned to penetrate pierceable membrane 258 when tubular sleeve 208 is moved upwardly into said first position. In this regard, pin 204 includes aperture 210 and lumen 212 extending therethrough for the passage of liquid when sleeve 208 is in said first position, or thereafter.

A particularly unique feature of in-line sleeve valve 200 is the construction of flexible flange 220, concentrically disposed between tubular port 202 and reciprocating tubular sleeve 208. Flexible flange 220 is sealed about its periphery to flange 222 of tubular port 202. This embodiment of flange 220 is preferably constructed of a resilient plastic material and is therefore relatively inexpensive. Flexible flange 220 includes weakened portions 224 and 226 which serve as flexible hinges so as to allow the reciprocating motion of tubular sleeve 208.

A variation on this embodiment may be seen in FIGS. 8 and 9. Tubular port 202 contains stationary plug 214, positioned for sealable engagement with reciprocating tubular sleeve 208. Resilient flexible flange 220 again has hinges 224 and 226 integrally formed therein, to allow the reciprocating motion of sleeve 208. However, at the periphery of flange 220 is a vertical collar 230 which is sealed to downwardly descending rim 232 of tubular port 202. This construction facilitates assembly of the components required. A perspective view of the components may be seen in FIG. 9, with inline valve 200 positioned for insertion into fill port 250 of a liquid container.

OPERATION OF THE INVENTION

In some applications, such as medical liquids in general and continuous ambulatory peritoneal dialysis (CAPD), in particular, the patient must hook up his implanted catheter to a container such as a flexible bag of dialysis solution. The present technique utilized requires a piercing pin/diaphragm system. A combination on/off gripping clamp is required to provide a gripping means to prevent the hand from contaminating the port during piercing of a bag of dialysate solution. In the embodiment illustrated in FIGS. 1 and 2, pulling of tubular sleeve 18 opens it to the flow of liquid within chamber 120. When released, flexible flange 20 causes tubular sleeve 18 to return against stationary plug 14. Pushing of tubular sleeve 18, particularly at grip 68, causes first end 66 of tubular sleeve 18 to pass over ribs 26 and be press-fit onto stationary plug 14, thereby sealing. Valve 50 is opened with a simple pulling action and closed with a pushing action. Piercing pin 60 is used to penetrate membrane 58 without the possibility of contaminating liquid 72. Additionally, upon emptying of bag 70, valve 50 may be resealed simply by pushing first end 66 over sealing rim 64, thereby shutting off the flow of liquid.

The foregoing description and drawings merely explain and illustrate the invention, and the invention is not limited thereto, except insofar as the appended claims are limited by those skilled in the art who have the disclosure before them and are able to make modifications and variations therein without departing from the scope of the invention.

I claim

1. An improved in-line sleeve valve comprising:
   a modular tubular port member;
   a stationary plug member affixed to and supported with said port member by a plurality of support members;
   a reciprocating tubular sleeve member constructed and arranged for sealable telescopic engagement with said stationary plug member in a first position, and for the passage of liquid therethrough in a second position; and
   resilient flexible flange means disposed between said reciprocating tubular sleeve and said modular tubing port member so as to seal the connection therebetween, said flange means being sufficiently elastic to allow easy manual displacement of said tubular sleeve from said stationary plug in order to allow the flow of liquid, but also being biased in a first direction so as to return said tubular sleeve to said first position abutting said stationary plug upon the release thereof;
   said resilient flange means comprising an integrally formed flanged member extending from said tubular sleeve member and having a distal connecting portion connected to said tubular port and a proximal portion extending between said tubular sleeve and said connecting portion, said flange member having an integrally formed hinge between said tubular sleeve and said proximal portion, and an integrally formed hinge between said connecting portion, said integrally formed hinges comprising a weakened portion of reduced thickness adjacent to said reciprocating tubular sleeve and said modular tubular port member which facilitate reciprocating movement of said tubular sleeve member, the remainder of said resilient flange means being of greater thickness than said weakened portion so as to provide sufficient stiffness to said resilient flange so as to bias said flange in said first direction, whereby said tubular sleeve may be manually displaced from said stationary plug and returned thereto as required.

* * * * *

UNITED STATES PATENT AND TRADEMARK OFFICE
CERTIFICATE OF CORRECTION

PATENT NO. : 4,397,442
DATED : August 9, 1983
INVENTOR(S) : Mark E. Larkin

It is certified that error appears in the above—identified patent and that said Letters Patent is hereby corrected as shown below:

In FIG. 5, lower right-hand side, delete "56" and insert --55--.

Column 4, line 30, delete "10" and insert --50--.

Column 4, line 40, delete "56" and insert --55--.

Column 6, line 20, delete "26" and insert --27--.

Signed and Sealed this

Twentieth Day of December 1983

[SEAL]

Attest:

Attesting Officer

GERALD J. MOSSINGHOFF

Commissioner of Patents and Trademarks